United States Patent [19]

Collins et al.

[11] Patent Number: 4,685,450
[45] Date of Patent: Aug. 11, 1987

[54] ENDOSCOPE

[75] Inventors: Ian P. Collins, Welwyn; William J. Revell, Great Dunmow, both of England

[73] Assignee: Warner Lambert Technologies, Inc., Southbridge, Mass.

[21] Appl. No.: 898,737

[22] Filed: Aug. 15, 1986

Related U.S. Application Data

[63] Continuation of Ser. No. 670,974, Nov. 15, 1985, abandoned.

[30] Foreign Application Priority Data

Nov. 12, 1983 [GB] United Kingdom ............... 8330241

[51] Int. Cl.$^4$ .............................................. A61B 1/06
[52] U.S. Cl. .......................................... 128/4; 128/6; 354/62
[58] Field of Search ............... 128/4, 5, 6; 354/62, 354/195.1, 286; 350/255

[56] References Cited

U.S. PATENT DOCUMENTS

| | | | |
|---|---|---|---|
| 3,900,021 | 8/1975 | Makepeace et al. | 128/4 |
| 4,168,702 | 9/1979 | Ohshiro | 128/6 |
| 4,188,942 | 2/1980 | Fellberg | 128/6 |
| 4,264,167 | 5/1981 | Plummer | 354/62 |
| 4,323,304 | 5/1982 | Ishii | 128/6 |
| 4,403,605 | 9/1983 | Tanikawa | 128/6 |
| 4,404,964 | 9/1983 | Kambara | 354/62 |
| 4,414,608 | 11/1983 | Furihota | 354/62 |
| 4,439,030 | 3/1984 | Ueda | 354/62 |
| 4,478,212 | 10/1984 | Asano | 128/6 |

FOREIGN PATENT DOCUMENTS 2819357  11/1979  Fed. Rep. of Germany ......... 128/4

Primary Examiner—Gene Mancene
Assistant Examiner—John G. Weiss
Attorney, Agent, or Firm—Bachman & LaPointe

[57] ABSTRACT

An endoscope has an eyepiece with an optical system (16) comprising a series of lenses (18) housed in a sleeve (20) which is movable longitudinally in the endoscope casing for focusing an image. An adjusting ring (26) is rotated to adjust the position of the sleeve (20), to focus the image for viewing by the eye. For viewing of the image by a camera, an adaptor (38) is fitted on the end of the endoscope eyepiece. The adaptor (38) has a slot (44) which receives a fixed projection (36) and a movable projection (30) on the adjusting ring (26). Rotation of the adaptor (38) rotates the ring (26) and thereby shifts the sleeve to a predetermined longitudinal position suitable for viewing of the image by a camera.

5 Claims, 3 Drawing Figures

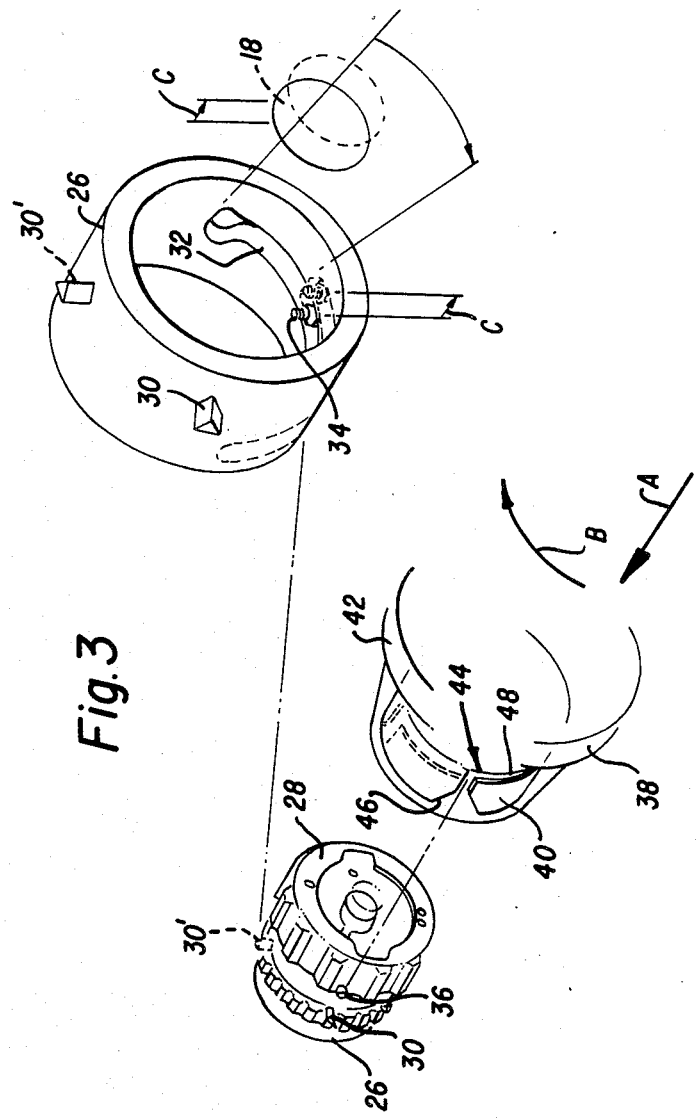

ENDOSCOPE

DESCRIPTION

This application is a continuation, of application Ser. No. 670,974, filed Nov. 15, 1985 abandon 10/16/86.

FIELD OF THE INVENTION

This invention relates to endoscopes, which are medical instruments for inspecting the cavities of internal organs.

BACKGROUND TO THE INVENTION

A typical form of known endoscope has a handle from which extends a flexible shaft terminating in a distal or operative end which is inserted into a body cavity to be inspected. Light is transmitted from the handle, through the shaft to the distal end where the light emitted illuminates the cavity to be inspected. The image to be viewed is transmitted back up the shaft to the handle which is equipped with an eyepiece for this purpose. The eyepiece includes a lens system which can be moved longitudinally by rotation of an adjusting ring in order to focus the image. For viewing the image by the eye, the user looks into the eyepiece and focuses the image for his eyesight by means of the adjusting ring.

It is desirable to have the facility of attaching a camera to the endoscope eyepiece, to enable the image to be photographed. The use of a camera requires that the image be brought into a predetermined position, even after the lens system has been adjusted to suit viewing by the eye. Hitherto this problem has been tackled by providing two adjusting rings each with a part-helical groove or cam track, one for adjusting the lens system for viewing by the eye and the other for adjusting the lens system for viewing by a camera.

The invention aims to provide a simpler arrangement requiring only one adjusting ring.

SUMMARY OF THE INVENTION

According to the invention an endoscope has an optical system for producing an image suitable to be viewed by the eye or alternatively by a camera, the optical system comprising a lens system movable longitudinally in a casing of the endoscope, and an adjusting ring which is rotatable with respect to the casing to adjust the position of the lens system for focusing and viewing of the image by the eye, wherein the endoscope is associated with a camera adaptor which is shaped so that when it is fitted on the endoscope casing the adaptor rotates the adjusting ring to a predetermined position corresponding to a desired predetermined position of the lens system suitable for viewing of the image by a camera. Hence, fitting of the camera adaptor to the endoscope automatically moves the adjusting ring to its predetermined position which positions the lens system so that the image is at the required position for the camera.

Preferably, the endoscope casing has a fixed projection and the adjusting ring carries a projection movable with the adjusting ring, the camera adaptor being shaped to locate with respect to both projections and engaging the movable projection to rotate the adjusting ring to the predetermined position. The camera adaptor may have a skirt-like wall provided with a slot which receives the fixed projection with a bayonet-like connection and which also receives the movable projection, the adaptor being fitted to the endoscope with the projections substantially aligned corresponding to viewing of the image by the eye. Thus, for viewing of the image by the eye the two projections are brought into substantial alignment which will focus the image for normal eyesight. The adjusting ring can be rotated slightly to suit the eyesight of a particular user. To fit the camera adaptor the two projections are brought into close alignment and the adaptor twisted onto the endoscope casing, this twisting movement rotating the adjusting ring to be predetermined position.

The slot may have a mouth portion leading into a circumferential portion, fitting of the camera adaptor to the endoscope casing aligning the fixed projection with the circumferential slot portion to enable the camera adaptor to be rotated with respect to the endoscope casing, and the movable projection being located in the mouth portion of the slot, so that rotation of the camera adaptor rotates the adjusting ring to the predetermined position.

The adjusting ring preferably has in its wall a slot into which projects a pin carried by the lens system, the slot being part-helical so that rotation of the ring effects longitudinal movement of the lens system with respect to the endoscope casing.

An endoscope according to the invention will now be described by way of example with reference to the accompanying drawings in which:

FIG. 1 is a fragmentary sectional view of the eyepiece end of the endoscope, showing the eyepiece in a condition for viewing of the image by the eye, FIG. 2 is a view corresponding to FIG. 1 but showing the eyepiece in a condition corresponding to camera viewing, and FIG. 3 is a diagrammatic view illustrating how the lens system is adjusted in position to suit camera viewing.

DETAILED DESCRIPTION OF THE DRAWINGS

Figure 1:
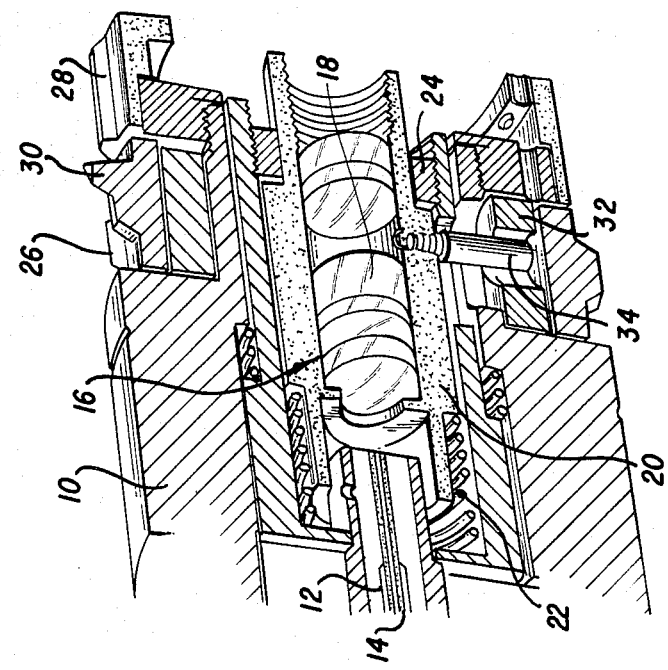
Figure 2:
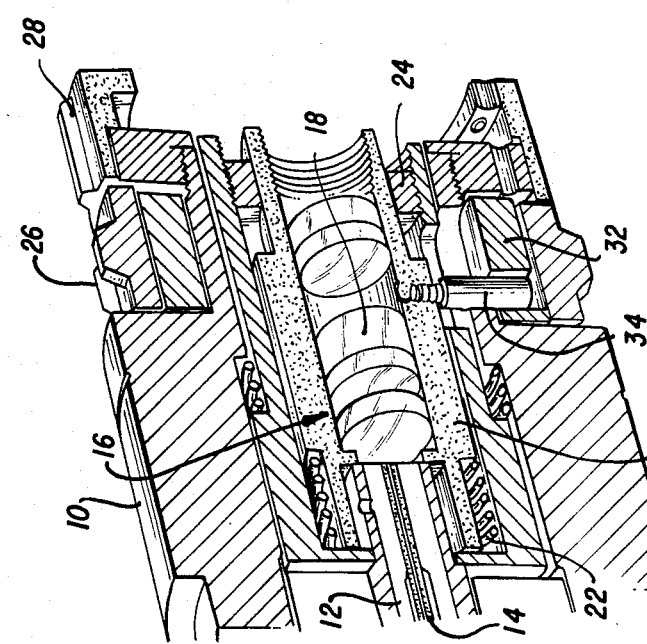

Referring to FIGS. 1 and 2, the endoscope has a handle casing 10 which encloses a sleeve 12 surrounding a fibre optic bundle 14 which transmits the image to be viewed from the distal end of the endoscope shaft (not shown) to an optical system 16 located in the handle. The optical system 16 comprises a series of lenses 18 housed in a sleeve 20 urged by a spring 22 into engagement with a screwed collar 24.

The casing 10 carries a rotatable adjusting ring 26 and, at the extreme end of the casing, a fixed ring 28. The adjusting ring 26 is rotatable with respect to the casing 10 and has on its outer periphery a projection 30 which is triangular in shape, as best seen in FIG. 3. The cylindrical wall of the adjusting ring 26 has a part-helical slot or cam track 32 into which projects a stud 34 projecting radially outwardly from and attached to the sleeve 20. As a result of the part-helical shape of the cam track 32, rotation of the adjusting ring 26 causes corresponding longitudinal or axial movement of the sleeve 20 and the lenses 18 carried thereby.

The fixed ring 28 carries an outwardly extending fixed projection 36 and the arrangement is such that when the projections 30 and 36 are aligned (FIG. 3) the optical system focuses the image in a position suitable for viewing of the image by the eye. Small adjustment of the adjusting ring 26 enables the image to be brought into sharp focus for any particular user. When the projections 30 and 36 are aligned the sleeve 20 is in the retracted position shown in FIG. 1.

To enable the image to be viewed by a camera the endoscope is associated with a camera adaptor shown at 38 in FIG. 3. The adaptor 38 is generally annular, having a skirt-like wall 40 for fitting to the endoscope and a cylindrical wall 42 provided with conventional means for attachment of the camera (not shown). The wall 40 is formed with a slot 44 having a flared mouth portion 46 leading into a circumferential portion 48.

The adaptor 38 is fitted to the endoscope by offering up (arrow A) the wall 40 to the eyepiece end of the endoscope with the two projections 30 and 36 in alignment, as shown in FIG. 3. The two projections 30 and 36 enter the slot 44, the fixed projection 36 being at one end of the circumferential slot portion 48 and the movable projection 30 being located in the mouth portion 46. The adaptor 38 is then turned, as indicated by the arrow B, to attach the adaptor 38 to the endoscope with a bayonet-like action. During this rotation the circumferential portion 48 moves over the fixed projection 36, whilst the movable projection 30 is rotated to a new position 30' shown in FIG. 3.

This rotation of the adjusting ring 26 causes the sleeve 20 to move to its extended position shown in FIG. 2. The amplitude of longitudinal movement of the lenses 18 is shown at C in FIG. 3. In this extended position the optical system occupies a predetermined axial position suitable for viewing of the image by the camera. the adaptor 38 is removed from the endoscope by rotation in a direction opposite to that of arrow B and subsequent withdrawal in a direction opposite to arrow A, leaving the endoscope in a condition suitable for viewing by the eye.

It will be appreciated that fitting of the adaptor 38 automatically brings the lens system into a position suitable for camera viewing, the extreme end of the circumferential portion 48 of the slot 44 having a "dead" length to take out tolerances.

We claim:

1. A method of focusing an endoscope for the purpose of photographing the endoscope field of view comprising the steps of:
   providing an camera,
   providing an endoscope having a handle casing, an adjustable lens system including an eyepiece mounted within the casing, and an adjusting ring rotatably carried by the casing and operatively connected to the lens system to permit rotation of the adjusting ring relative to the casing between a first position at which the field of view of the endoscope is focused for viewing with the eye and a second position at which said field of view is focused for photographing with the camera,
   positioning the adjusting ring in said first position,
   providing a coupling for connecting the endoscope to the camera wherein the coupling includes an annular body having one end adapted to be coupled to a camera and another end adapted to accept a portion of the casing and be releasably attached thereto as said another end is operatively positioned about the casing and rotated relative thereto between a release condition at which the coupling can be removed from the casing and a fully locked condition, the coupling and the adjusting ring including means joining the adjusting ring to the annular body and cooperating with one another so that when said another end of the annular body is positioned about the casing and the annular body is rotated relative to the casing between said release and fully locked conditions, the adjusting ring is rotated between said first and second positions, and
   operatively positioning said another end of the coupling annular body about the casing and rotating the body relative to the casing from said release to said fully locked conditions to thereby rotate the adjusting ring from said first to said second positions.

2. In combination,
   an endoscope having a handle casing, an adjustable lens system including an eyepiece mounted within the casing, and an adjusting ring rotatably carried by the casing and operatively connected to the lens system to permit rotation of the adjusting ring relative to the casing between a first position at which the field of view of the endoscope is focused for viewing with the eye and a second position at which said field of view is focused for photographing with a camera, and
   a coupling for connecting the endoscope to a camera for the purpose of photographing the field of view of the endoscope, the coupling including an annular body having one end adapted to be coupled to a camera and another end adapted to acept a portion of the casing and be releasably attached thereto as said another end is operatively positioned about the casing and rotated relative thereto between a release condition at which the coupling can be removed from the casing and a fully locked condition, the coupling and the adjusting ring including means joining the adjusting ring to the annular body and cooperating with one another so that when said another end of the annular body is positioned about the casing and the annular body is rotated between said release and fully locked conditions, the adjusting ring is rotated between said first and second positions.

3. The combination of claim 2 wherein the casing carries a first projection and the adjusting ring carries a second projection, the coupling including means for engaging the second projection and rotating the adjusting ring from said first position to said second condition as the coupling is rotated from said release condition to said fully locked condition and for cooperating with the first projection to releasably lock the coupling to the endoscope when the coupling is rotated to said fully locked condition.

4. The combination of claim 3 wherein said first and second projections are generally positioned in alignment with one another when the adjusting ring is positioned in said first position and said coupling defines a skirt-like wall provided with a slot for receiving both the first and second projection and cooperates with the first projection for connecting the coupling to the casing in a bayonet-like connection.

5. The combination of claim 4 wherein the slot defines a mouth portion for accepting the aligned first and second projections when the coupling is operatively placed about the casing and joining the second projection to the coupling for movement therewith between said release and fully locked condition and a circumferential slot portion for accepting the first projection so that as the coupling is rotated between said release and fully locked conditions, the first projection is guided along the slot portion.

* * * * *